US009161716B2

(12) United States Patent
Estocado

(10) Patent No.: US 9,161,716 B2
(45) Date of Patent: Oct. 20, 2015

(54) DIAGNOSTIC IMAGING SYSTEM FOR SKIN AND AFFLICTION ASSESSMENT

(71) Applicant: N.E. SOLUTIONZ, LLC, Las Vegas, NV (US)

(72) Inventor: Nancy A. Estocado, Las Vegas, NV (US)

(73) Assignee: N.E. SOLUTIONZ, LLC, Las Vegas, NV (US)

( * ) Notice: Subject to any disclaimer, the term of this patent is extended or adjusted under 35 U.S.C. 154(b) by 253 days.

(21) Appl. No.: 13/964,278

(22) Filed: Aug. 12, 2013

(65) Prior Publication Data

US 2013/0331708 A1    Dec. 12, 2013

Related U.S. Application Data

(63) Continuation-in-part of application No. 13/531,527, filed on Jun. 23, 2012, now Pat. No. 8,505,209, which is a continuation-in-part of application No. 12/606,773, filed on Oct. 27, 2009, now Pat. No. 8,276,287.

(51) Int. Cl.
*A61B 5/00* (2006.01)
*A61B 5/107* (2006.01)
*G01B 3/04* (2006.01)

(52) U.S. Cl.
CPC .............. *A61B 5/441* (2013.01); *A61B 5/0077* (2013.01); *A61B 5/1072* (2013.01); *A61B 5/444* (2013.01); *A61B 5/445* (2013.01); *A61B 5/743* (2013.01); *G01B 3/04* (2013.01)

(58) Field of Classification Search
CPC ............. A61B 5/00; A61B 5/107; A61B 6/00
USPC .......... 33/511, 512, 679.1; 600/300, 477, 587
See application file for complete search history.

(56) References Cited

U.S. PATENT DOCUMENTS 898,565 A    9/1908   Duncan
999,425 A    8/1911   Zaino (Continued)

FOREIGN PATENT DOCUMENTS

DE    3622073 A      1/1988
JP    2003000568 A   1/2003
WO    2005002438 A1  1/2005

OTHER PUBLICATIONS

EPO Appln. No. 10828796.2, Extended European Search Report, Jul. 23, 2014, 6 pg.

(Continued)

*Primary Examiner* — Yaritza Guadalupe-McCall
(74) *Attorney, Agent, or Firm* — Cuenot, Forsythe & Kim, LLC

(57) ABSTRACT

A captured image is received depicting at least a portion of an assessment tool and an affliction to which the assessment tool is proximally located. An assessment image is generated from the captured image and configured to be presented on a display, the assessment image including at least a portion of the captured image including the portion of the assessment tool and the affliction to which the assessment tool is proximally located. The assessment tool includes at least a first arm depicting measurement indicators to which a size of the affliction is correlated. The captured image is processed to identify at least one dimension of the affliction. The dimension is compared to the measurement indicators depicted on the first arm of the assessment tool to determine the size of the affliction.

20 Claims, 14 Drawing Sheets

(56) References Cited

U.S. PATENT DOCUMENTS

| | | | |
|---|---|---|---|
| 1,121,289 A | 12/1914 | Robertson | |
| 1,663,895 A | 3/1928 | Wolfe et al. | |
| 1,763,091 A | 6/1930 | Cangemi | |
| 1,776,393 A | 9/1930 | Onorato | |
| 1,904,234 A | 4/1933 | Morine et al. | |
| 2,503,398 A | 4/1950 | Lindsey | |
| 2,720,707 A | 10/1955 | Bickley | |
| 2,928,182 A | 3/1960 | Malczewski | |
| 3,245,882 A | 4/1966 | Guthrie | |
| 3,559,881 A | 2/1971 | Maison | |
| 3,819,490 A | 6/1974 | Klingstrom et al. | |
| 4,097,997 A | 7/1978 | Bjornson | |
| 4,279,259 A | 7/1981 | Lee et al. | |
| 4,389,782 A | 6/1983 | Webster | |
| 4,420,891 A | 12/1983 | Orem | |
| 4,483,075 A | 11/1984 | Kundin | |
| 4,517,747 A | 5/1985 | Morin | |
| 4,969,271 A | 11/1990 | Sump | |
| 5,014,438 A | 5/1991 | Gravel | |
| 5,018,531 A | 5/1991 | Hartman | |
| 5,163,228 A | 11/1992 | Edwards et al. | |
| 5,167,076 A | 12/1992 | Sump | |
| 5,170,570 A | 12/1992 | Mays, Jr. | |
| 5,265,605 A | 11/1993 | Afflerbach | |
| 5,534,952 A | 7/1996 | Zanecchia et al. | |
| 5,605,165 A | 2/1997 | Sessions et al. | |
| 5,678,317 A | 10/1997 | Stefanakos | |
| 5,741,212 A | 4/1998 | Matthews | |
| 5,969,822 A | 10/1999 | Fright et al. | |
| 6,026,579 A | 2/2000 | Autrey | |
| 6,159,167 A | 12/2000 | Hardin-Naser | |
| 6,351,893 B1 | 3/2002 | St. Pierre | |
| 6,408,529 B1 | 6/2002 | Hodges | |
| 6,471,661 B1 | 10/2002 | Burns | |
| 6,540,756 B1 | 4/2003 | Vaughan | |
| 6,725,559 B2 | 4/2004 | Burt, Jr. | |
| 6,993,851 B2 | 2/2006 | Cohen | |
| 7,376,456 B2 | 5/2008 | Marshik-Geurts et al. | |
| 7,401,413 B1 | 7/2008 | Nelson | |
| 7,412,780 B2 | 8/2008 | Holder | |
| 7,421,789 B1 | 9/2008 | Sullivan | |
| 7,614,155 B2 | 11/2009 | Healey | |
| 7,975,395 B2 | 7/2011 | Keller et al. | |
| 8,176,647 B2 | 5/2012 | Masley et al. | |
| 8,276,287 B2 | 10/2012 | Estocado | |
| 8,505,209 B2 | 8/2013 | Estocado | |
| 2003/0213140 A1 | 11/2003 | Burt, Jr. | |
| 2004/0059199 A1* | 3/2004 | Thomas et al. | 600/300 |
| 2004/0107592 A1 | 6/2004 | Matlis | |
| 2004/0134084 A1 | 7/2004 | Vanneste | |
| 2006/0005409 A1 | 1/2006 | Cohen | |
| 2006/0032068 A1 | 2/2006 | Sherman et al. | |
| 2006/0075647 A1 | 4/2006 | Garrick | |
| 2007/0157483 A1 | 7/2007 | DuMais | |
| 2007/0240321 A1 | 10/2007 | Shapiro | |
| 2008/0194928 A1* | 8/2008 | Bandic et al. | 600/306 |
| 2008/0234552 A1 | 9/2008 | Averbach | |
| 2008/0289199 A1 | 11/2008 | Healey | |
| 2009/0013546 A1 | 1/2009 | Keller et al. | |
| 2009/0119939 A1 | 5/2009 | Rosso et al. | |
| 2009/0126210 A1 | 5/2009 | Ball et al. | |
| 2009/0213213 A1 | 8/2009 | Fright et al. | |
| 2009/0253968 A1* | 10/2009 | Cho et al. | 600/301 |
| 2011/0098539 A1 | 4/2011 | Estocado | |
| 2012/0084990 A1 | 4/2012 | Masley et al. | |
| 2012/0270196 A1* | 10/2012 | Hettrick et al. | 434/262 |
| 2012/0323126 A1 | 12/2012 | Estocado | |
| 2013/0346095 A1 | 12/2013 | Buckland | |

OTHER PUBLICATIONS

Russell, L., "The Importance of Wound Documentation and Classification," British Journal of Nursing, Allen, London, GB, vol. 8, No. 20, Jan. 1, 1999, pp. 1342-1354.

Fette, A.M., "A Clinimetric Analyisis of Wound Measurement Tools," [onlilne] World Wide Wounds, Jan. 19, 2006 [retrieved Jul. 7, 2014] retrieved from the Internet: <http://www.worldwisdewounds.com/2006/January/Fette/Clinimetric-Analysis-Wound-Measurement-Tools.html>, 7 pg.

Patent Cooperation Treaty, "PCT Search Report and Written Opinion of the International Searching Authority," for International Application PCT/US2010/053559, Jun. 3, 2011, 8 pages.

Aranz Medical Ltd., Silhouette Mobile Product Sheet, 2006.

Bosio, et al., "A Proposal for Classifying Peristomal Skin Disorders: Results of a Multicenter Observational Study," Ostomy Wound Management, vol. 53, No. 9, pp. 38-43, Sep. 1, 2007.

* cited by examiner

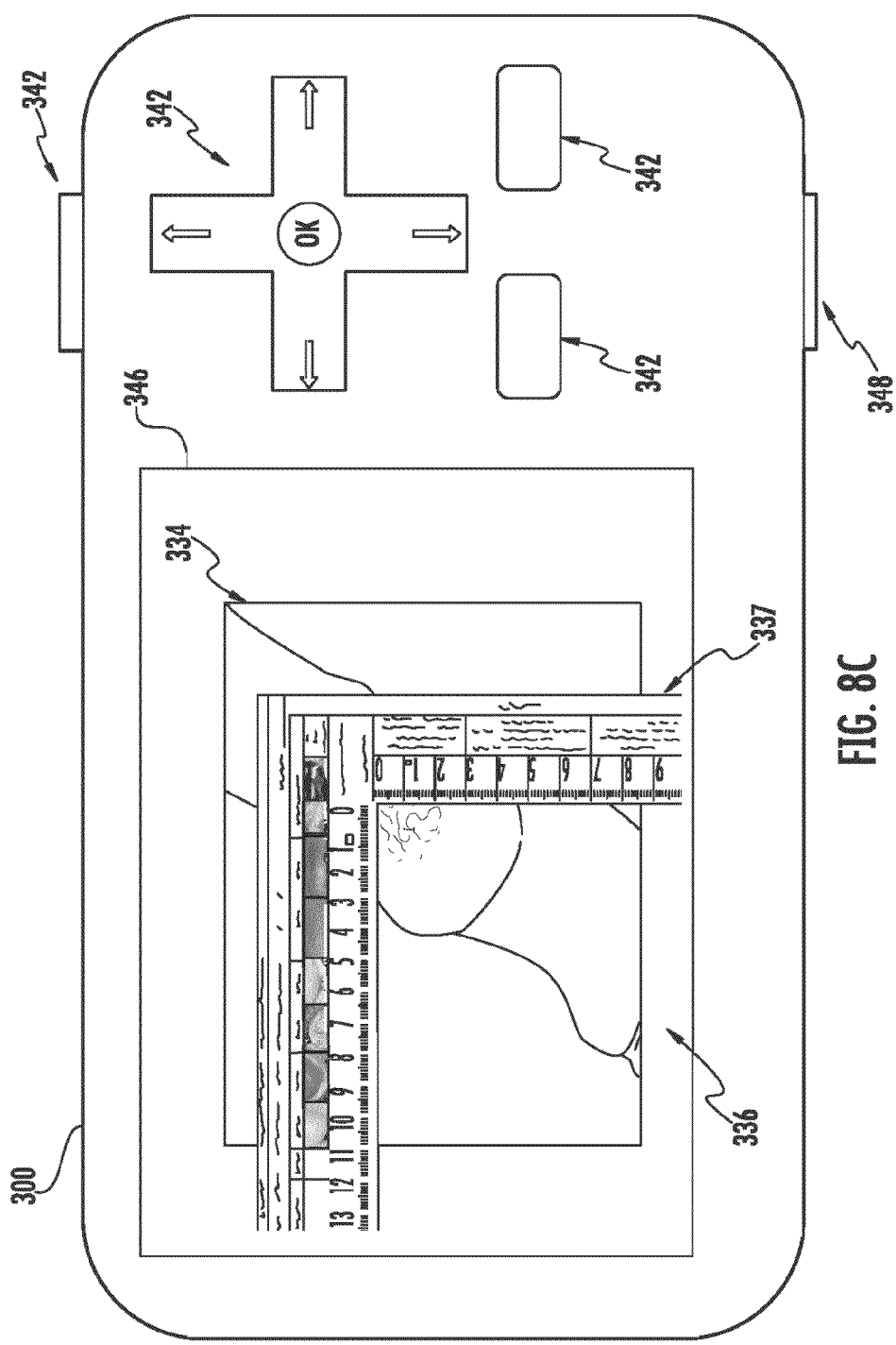

DIAGNOSTIC IMAGING SYSTEM FOR SKIN AND AFFLICTION ASSESSMENT

CROSS-REFERENCE TO RELATED APPLICATIONS

This application is a continuation-in-part of U.S. application Ser. No. 13/531,527 filed Jun. 23, 2012, entitled SKIN AND WOUND ASSESSMENT TOOL, which is a continuation-in-part of U.S. application Ser. No. 12/606,773 filed Oct. 27, 2009, now U.S. Pat. No. 8,276,287 issued Oct. 2, 2012, entitled SKIN AND WOUND ASSESSMENT TOOL, the entirety of which is fully incorporated herein by reference.

COPYRIGHT AUTHORIZATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates generally to medical diagnostic tools.

BACKGROUND OF THE INVENTION

The accurate and consistent diagnosis of patient health parameters is essential for the proper staging and treatment of the patient. Consistency in measurement results over time for a single patient is vital to ensure that the actual progress or degradation of the health of the patient is being properly determined. Consistency in measurement results across patients is also vital to ensure that treatment protocols and their underlying data are applied consistently from patient to patient.

Many types of patient health criteria may be classified along a sliding scale depending upon the severity of the affliction. For example, burns have a classification scale of severity ranging from first degree (least severe) up to third degree (most severe). Other classification scales exist for other types of afflictions, such as the Wagner's Scale for foot ulcers, the Payne Martin Classification for skin tears, and the National Pressure Ulcer Advisory Panel (NPUAP) Pressure Ulcer Staging System. Each of these classification scales has a known and accepted classification system that permits a practitioner to assess an affliction against certain predefined standards and assign to the affliction a classification value corresponding to one of a plurality of ranks along the severity scale. Changes of this value in time thus correspond to improving or deteriorating conditions of the affliction and permit the rapid assessment of patient health and progress. It is therefore critical for staging and treatment purposes that clinicians be able to accurately and consistently assess an affliction and classify it into its proper rank along a known scale for that affliction.

BRIEF SUMMARY

One or more embodiments disclosed within this specification relate to diagnostic imaging systems and, more particularly, to a diagnostic imaging system for skin and affliction assessment.

A diagnostic imaging system includes a processor programmed to initiate executable operations. The executable operations include receiving a captured image depicting at least a portion of an assessment tool and an affliction to which the assessment tool is proximally located. The executable operations also include generating an assessment image from the captured image and configuring the assessment image to be presented on a display, the assessment image comprising at least a portion of the captured image including the portion of the assessment tool and the affliction to which the assessment tool is proximally located, the assessment tool comprising at least a first arm, the first arm depicting measurement indicators to which a size of the affliction is correlated. The executable operations further include processing the captured image to identify at least one dimension of the affliction and comparing the identified at least one dimension of the affliction to the measurement indicators depicted on the first arm of the assessment tool to determine the size of the affliction.

A method includes receiving a captured image depicting at least a portion of an assessment tool and an affliction to which the assessment tool is proximally located. The method also includes generating an assessment image from the captured image and configuring the assessment image to be presented on a display, the assessment image comprising at least a portion of the captured image including the portion of the assessment tool and the affliction to which the assessment tool is proximally located, the assessment tool comprising at least a first arm, the first arm depicting measurement indicators to which a size of the affliction is correlated. The method further includes processing the captured image to identify at least one dimension of the affliction and comparing the identified at least one dimension of the affliction to the measurement indicators depicted on the first arm of the assessment tool to determine the size of the affliction.

A computer program product includes a computer-readable storage medium having program code stored thereon. The program code is executable by a processor to perform a method. The method includes receiving a captured image depicting at least a portion of an assessment tool and an affliction to which the assessment tool is proximally located. The method also includes generating an assessment image from the captured image and configuring the assessment image to be presented on a display, the assessment image comprising at least a portion of the captured image including the portion of the assessment tool and the affliction to which the assessment tool is proximally located, the assessment tool comprising at least a first arm, the first arm depicting measurement indicators to which a size of the affliction is correlated. The method further includes processing the captured image to identify at least one dimension of the affliction and comparing the identified at least one dimension of the affliction to the measurement indicators depicted on the first arm of the assessment tool to determine the size of the affliction.

BRIEF DESCRIPTION OF THE DRAWINGS

FIGS. 8A-8C show back views of the diagnostic imaging system of FIG. 7 with image manipulation being performed by a user according to an assessment method in accordance with one embodiment disclosed within this specification.

DETAILED DESCRIPTION

Figure 1:
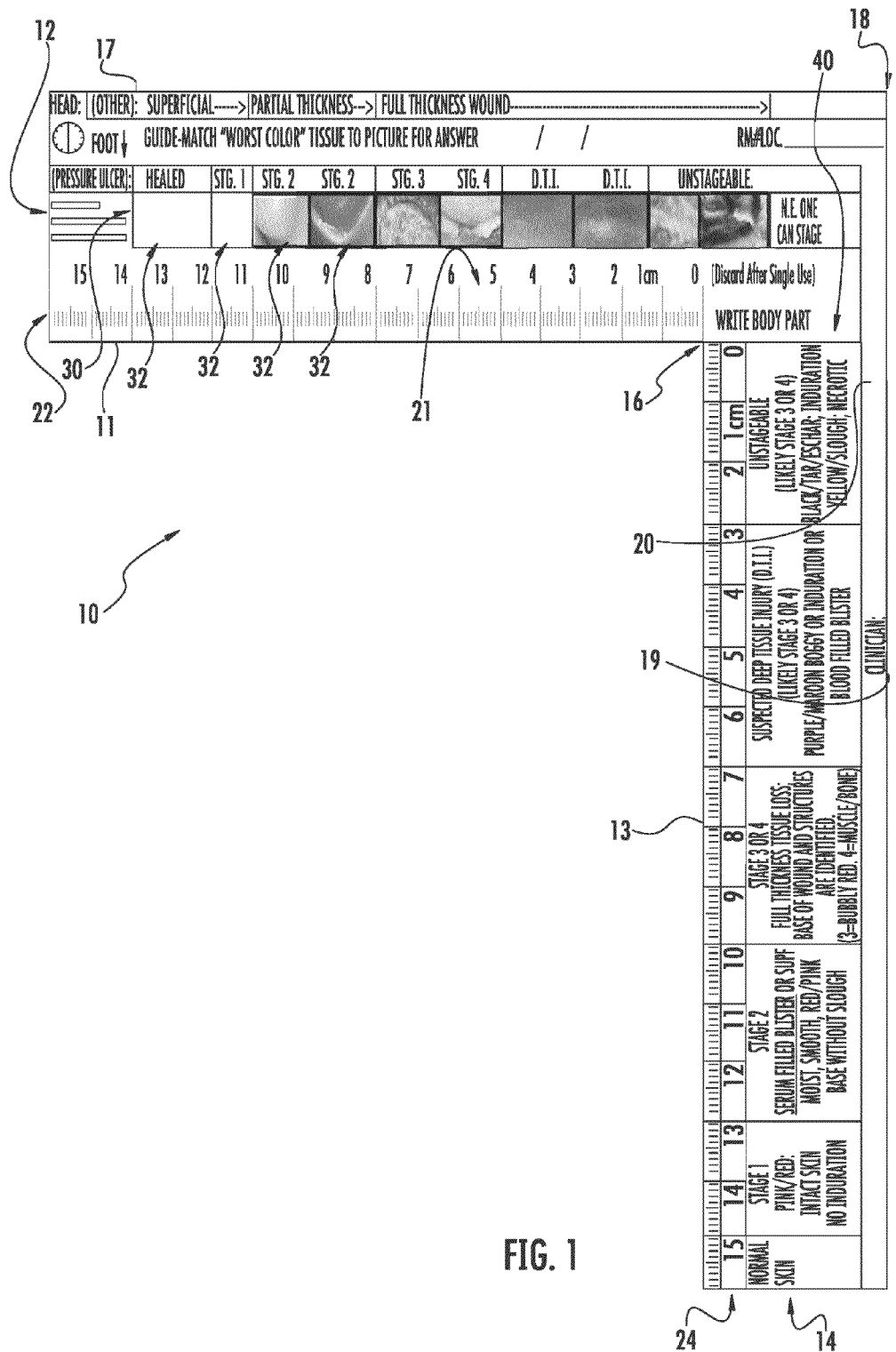
FIG. 1 is a top view of a diagnostic classification assessment tool in accordance with one embodiment disclosed within this specification.

While the specification concludes with claims defining features that are regarded as novel, it is believed that the claims will be better understood from a consideration of the description in conjunction with the drawings. As required, detailed embodiments are disclosed herein; however, it is to be understood that the disclosed embodiments are merely exemplary and can be embodied in various forms. Therefore, specific structural and functional details disclosed herein are not to be interpreted as limiting, but merely as a basis for the claims and as a representative basis for teaching one skilled in the art to variously employ virtually any appropriately detailed structure. Further, the terms and phrases used herein are not intended to be limiting but rather to provide an understandable description.

Several definitions that apply throughout this document will now be presented.

As used herein, a "subject" is any person, animal, plant, system or the like upon which measurements may be made. A subject may be referred to herein as a "patient."

As used herein, an "affliction" broadly includes a wound, skin abnormality, blemish, disease, state or condition exhibited by a subject that may exhibit one or more measurable symptoms or characteristics.

As used herein, a "clinician" or "practitioner" is a person that takes measurements of a subject, and may include a doctor, nurse, physical therapist, laboratory personnel or the like.

As used herein, a "value" includes a number, letter, symbol, word or the like.

As used herein, a "classification system" is an assessment procedure that permits a clinician to assign a value to an affliction based upon one or more measurable symptoms or characteristics. Each value corresponds to one of a plurality of ranks, each rank being associated with a predefined state or condition of the affliction. Ranks, and their corresponding values, are typically ordered by severity or the like. By way of example, classification systems include the burn classification system, the Wagner's Scale for foot ulcers, the Payne Martin Classification for skin tears, the NPUAP pressure ulcer staging system, the Center for Disease Control (CDC) Surgical Wound Classifications, Bruise Classification, Primary Lesions and Secondary Lesions.

As used herein, the term "affliction classifier" means a user selectable or user input value assigned to an affliction and representing one or more symptoms or characteristics of the affliction in a classification system.

As used herein, "rank classifier indicia" include one or more symptoms or characteristics of an affliction when in a state or condition corresponding to a rank. Rank classifier indicia may be indicated graphically through illustrations, photographs and the like, as well as textually.

As defined herein, the term "computer-readable storage medium" means a tangible computer-readable device or recording medium into which data can be copied and held until some later time, and from which the data can be obtained. As the term "computer-readable storage medium" is used herein, and consistent with its usage by those skilled in the art, a "computer-readable storage medium" does not include a transitory, propagating signal per se.

Specific reference is made in the following to the medical fields, for which particularly preferred embodiment devices are adapted, but it should be understood that other embodiment devices may be more widely employed and may not be limited to only the field of medical assessment.

As known in the field of assessments and diagnostics, and in the medical fields in particular, afflictions of a specific type may be encountered in wide degrees of various states of intensity or severity. Predefined classification systems exist that permit a clinician or practitioner to "pigeon hole" a patient's affliction into a rank based upon severity and thereby record a corresponding value into the patient's chart. Each rank in the classification system is typically characterized by corresponding rank classifier indicia that clinicians or practitioners are familiar with and against which clinicians or practitioners compare the affliction to determine the corresponding rank.

FIG. 1 is a top view of a diagnostic classification assessment tool (hereinafter "tool") 10 in accordance with one embodiment disclosed within this specification. The tool 10 permits rapid, accurate and repeatable rank determinations by clinicians or other users of the tool 10. By way of specific example, the tool 10 can be configured to permit the classification skin tissue wounds. It will be appreciated that tools configured to permit the classification of other types of afflictions are possible. Skin pressure ulcer wounds are typically classified into six or more ranks. These ranks may be ordered by the severity of the skin tissue wound and include, in order, healed (or closed), pre-stage 1 and stages one to four, suspected deep tissue injury (DTI), and unstageable. "Healed" or closed is the degenerate case in which there is no tissue wound or there is normal skin closed skin, and the corresponding rank classifier indicia would be those characteristics of skin that are normal, resurfaced, repaired-scarred, etc.

Rank classifier indicia for pre-stage I wounds include intact skin with localized, blanchable redness that is typically over a bony prominence.

Rank classifier indicia for stage I wounds include intact skin with localized, non-blanchable redness that is typically over a bony prominence. It is noted that with respect to darkly pigmented skin, the corresponding stage I rank classifier indicia may not include visible blanching, although the color of the wound may differ from the surrounding area. Additional stage I rank classifier indicia pain in the area, or the area being softer, warmer or cooler than the surrounding tissue.

Corresponding rank classifier indicia for stage II wounds include a partial loss of thickness of the dermis, which presents as a shallow open ulcer having a smooth reddish or pinkish wound bed, but the wound itself presents without slough. Stage II rank classifier indicia may also include an open or ruptured, serum-filled blister. Additional stage II rank classifier indicia include a shiny or dry, shallow ulcer without slough or bruising.

Stage III rank classifier indicia may include full thickness tissue loss, including visible subcutaneous fat, and/or moist, red, bubbly granulation tissue, but not including exposed visible bone, tendon or muscle. Sloughing may be part of stage III rank classifier indicia so long as it does not obscure the depth of tissue loss. Undermining and tunneling are also suitable rank classifier indicia. It will be appreciated that rank classifier indicia may vary depending upon the location of the affliction upon the subject. For example, the depth of a stage III pressure ulcer may vary by anatomical location, and thus corresponding rank classifier indicia may include anatomical position in the context of other symptoms or characteristics.

Stage IV rank classifier indicia include full thickness tissue loss with exposed bone, tendon or muscle. Other rank classifier indicia include slough or eschar in some regions of the wound bed. Undermining and tunneling may also be suitable stage IV rank classifier indicia.

DTI rank classifier indicia include intact skin with purple, maroon or the like coloration, or a blood-filled blister arising from damaged underlying soft tissue arising from pressure, shear or both. Additional rank classifier indicia include pain, or tissue that is firmer, cooler, or warmer, than the adjacent tissue, or that is mushy or boggy. Suitable rank classifier indicia may not be pronounced or obvious in subjects with dark skin tones. Additional rank classifier indicia may include the evolution of the wound, and in particular a thin blister over a dark wound bed that evolves to become covered by thin eschar.

Rank classifier indicia for the unstageable rank include full thickness tissue loss in which the base of the ulcer is covered by slough (which may be yellow, tan, gray, green or brown) and/or eschar (which may be tan, brown or black) in the wound bed. This ranking may be used as a placeholder until enough slough and/or eschar is removed to expose the base of the wound, after which the true depth, and therefore proper stage as characterized above, of the wound may be determined.

Referring again to FIG. 1 in the context of the above described rank classifier indicia. In one arrangement, the tool 10 can be L-shaped, having a first arm 12 and a second arm 14 that meet at a right angle. An internal origin 16 and an external origin 18 are thereby respectively created by the meeting of the first arm 12 and second arm 14. More specifically, the internal origin 16 is formed by the intersection of the respective internal edges 11 and 13 of the first arm 12 and the second arm 14. Similarly, the external origin 18 is formed at the intersection of the respective external edges 17 and 19 of the first arm 12 and the second arm 14. In another arrangement, the tool 10 need not be L-shaped. For example, the first arm 12 and the second arm 14 can meet an angle that is not a right angle. Moreover, in lieu of the tool 10 having the internal origin 16, the internal edges 11 and 13 of the tool 10 can be joined using a curved edge, or radius.

The tool 10 is formed from a substrate 20 having a top surface 21 and a bottom surface. The top surface 21 is shown in FIG. 1. The substrate is preferably made from a clean, disposable, single patient use material. More preferably, the substrate 20 is made from paper. In certain preferred embodiments the tool 10 meets the requirements for using "clean technique" versus "sterile technique" procedures due to the fact that most wounds are contaminated and thus do not require the more stringent sterile technique protocols. However, other arrangements of the tool 10 may conform to such "sterile technique" protocols to accommodate, for example, new incision-type wounds made in an operating room, or to accommodate tools 10 placed within a sterile packaging kit, as may be done, for example, with negative wound therapy dressing kits. Tools 10 may therefore be manufactured in accordance with sterile technique methods in a certified sterilization facility and may thus be used, packaged and labeled per national standards. However, other or additional substrate 20 materials are possible, such as coating the top surface, bottom surface or both of the tool 10 with antimicrobial or antiseptic agents, such as Silver AG+, Hydroferra Blue, Chlorhexidine Gluconate, Dakins, Acetic Acid, Betadine, Aluminum Salts and the like. The tool 10 may also be laminated with an approved-see through covering that may be disinfected between patient use.

Figure 2:
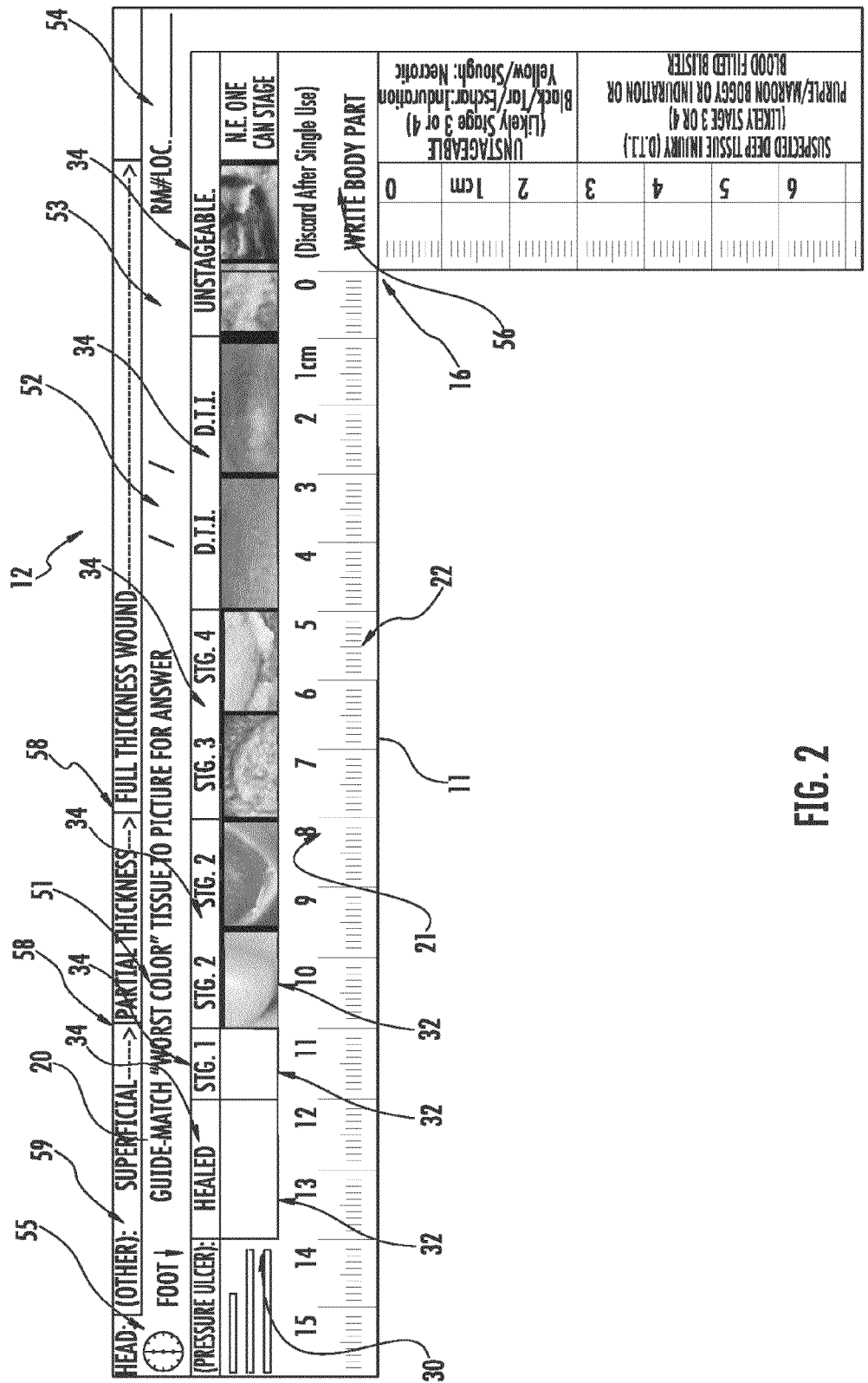
FIG. 2 is a detailed view of a first arm of the device shown in FIG. 1.

A detailed view of the top surface 21 of the first arm 12 is shown in FIG. 2. The top surface 21 of the first arm 12 may include a first ruler 22, which is preferably immediately adjacent to, and runs along, the internal side 11. The first ruler 22 may be formed by any suitable means, but is preferably formed by ink markings. The origin (or zero-point) of the first ruler 22 may be advantageously aligned with the internal origin 16.

The top surface 21 of the first arm 12 also includes a graphical ranking guide 30. The graphical ranking guide 30 includes a plurality of graphical images 32, which are preferably color photographs or color illustrations, although it will be appreciated that any suitably clear, representative images as discussed in the following may be utilized. Color images are highly preferred, however, as they uniquely and intuitively provide color information that may be highly relevant to rank classifier indicia. Color graphical images 32 provide the unappreciated benefit of more consistent and reproducible affliction rank classifications by practitioners, which is highly desirable for patient health and treatment purposes. Each graphical image 32 corresponds to a rank in the classification system for the affliction to be diagnosed with the aid of tool 10. Each rank in the classification system is preferably provided at least one corresponding graphical image 32, and as shown in FIGS. 1 and 2 may in some cases include two or more representative images 32. Each graphical image 32 graphically presents to the practitioner rank classifier indicia representative for that rank corresponding to the image 32. Adjacent to each graphical image 32, or groups of graphical images 32, may be a corresponding rank title indicator 34, which indicates the name of that rank for the corresponding graphical image(s) 32. By way of example, below rank title indicator 34 "Healed" (or Closed) is a graphical image 32 of skin that is normal, resurfaced, repaired-scarred, etc., which corresponds to the "Healed" rank for the wound classification system employed by the tool 10. Similarly, two graphical images 32 are shown, each corresponding to a stage two wound, above each of which is provided the rank title indicator 34 "STG. 2", indicating the rank of stage two. In the same vein, graphical images 32 are provided for stages one, three and four, as well as DTI and unstageable wounds, for each of which is further included a corresponding rank title indicator 34.

Figure 3:
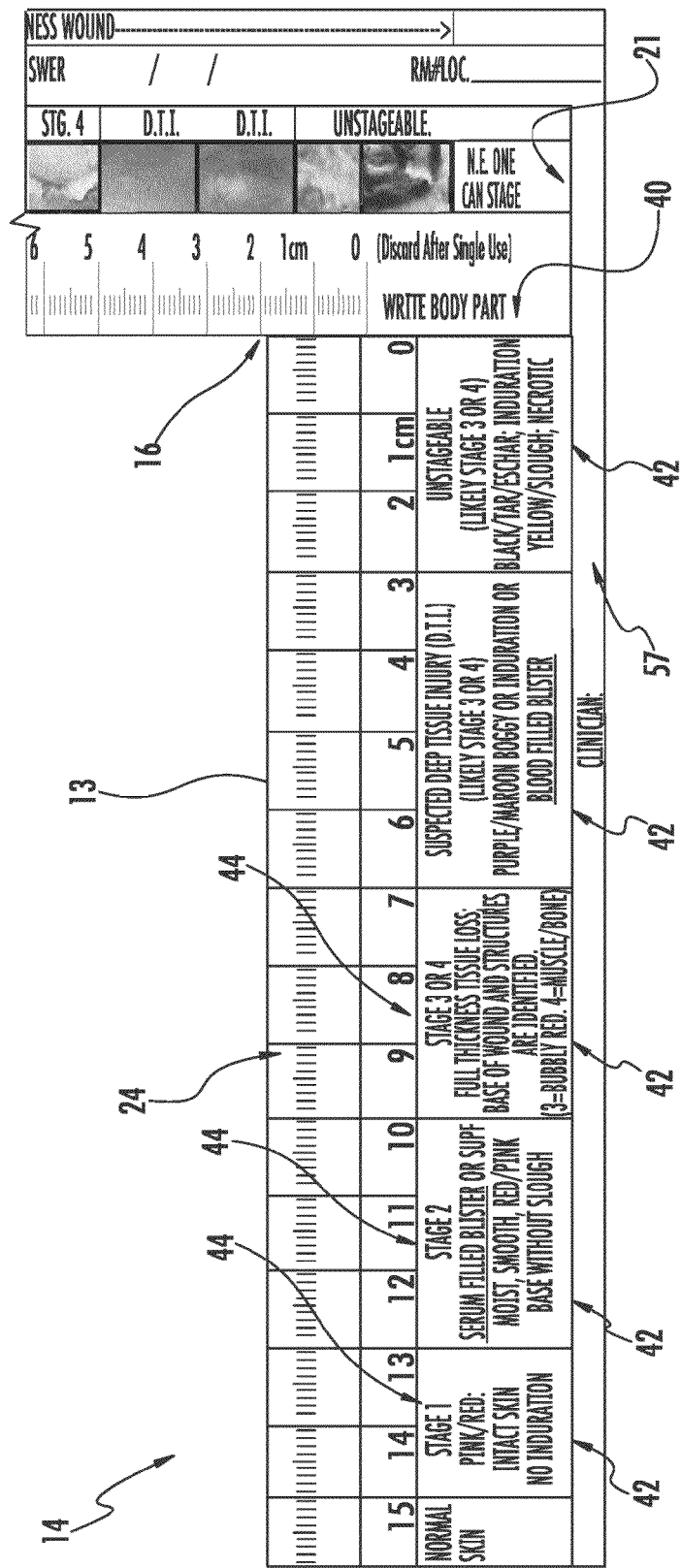
FIG. 3 is a detailed view of a second arm of the device shown in FIG. 1.

A detailed view of the top surface 21 of the second arm 14 is shown in FIG. 3. The top surface 21 of the second arm 14 may include a second ruler 24, which is preferably immediately adjacent to, and runs along, the internal side 13 of the second arm 14. The second ruler 24 may be formed in the same manner as the first ruler 22. The origin (or zero-point) of the second ruler 24 may be advantageously aligned with the internal origin 16. The first ruler 22 and the second ruler 24 thus provide a convenient Cartesian coordinate system that may be used to measure, for example, the area of an affliction, the extent of the affliction along the first arm 12, and the extent of the affliction along the second arm 14.

The top surface 21 of the second arm 14 also includes a descriptive ranking guide 40. The descriptive ranking guide 40 includes a plurality of rank descriptors 42 that contain text describing the salient features of the respective rank classifier indicia for that rank. Each rank descriptor 42 corresponds to a rank in the classification system for the affliction to be diagnosed with the aid of tool 10. Each rank in the classification system is preferably provided at least one corresponding rank descriptor 42, but in some cases two or more ranks may share portions of a common rank descriptor 42, as shown in FIGS. 1 and 3. Each rank descriptor 42 has text that describes to the practitioner the most significant rank classifier indicia that is representative for that rank or group of ranks corresponding to the descriptor 42. Adjacent to, or with, each rank descriptor 42 may be a corresponding rank title indicator 44, which indicates the name of that rank, or group of ranks, for the corresponding rank descriptor 42. By way of example, below rank title indicator 44 "Stage 3 or 4" is text describing the most salient features common to Stage 3 ranked and Stage 4 ranked afflictions in the wound classification system; also included are descriptors that are respectively specific to Stage 3 ranked afflictions and Stage 4 ranked afflictions. In contrast, Stage 1 and Stage 2 ranks each have their own rank descriptor 42 and corresponding rank title indicators 44.

As shown in FIGS. 2 and 3 the tool 10, and preferably the top surface 21 of the tool 10, may include additional information, and in particular may include lines, boxes or forms that may be filled in by the practitioner. For example, the tool 10 may include brief instructions for use 51, a date field 52, a subject initial field 53, a subject location field 54, an anatomical position (the tool 10 is preferably positioned at 12 O'clock on the subject to standardize the method) field 55, an affliction location (body part) field 56 (i.e., where the affliction is located on the subject), a field for the name of the practitioner 57 and so forth.

It will be appreciated that the embodiment tool 10 is not limited to merely one categorization system. It is possible, for example, to provide the first arm 12 with a graphical ranking guide and corresponding descriptive ranking guide for a first classification system, and provide the second arm 14 with a graphical ranking guide and corresponding descriptive ranking guide for a second classification system. Variations on this theme are also possible. By way of specific example, the embodiment tool 10 includes the graphical ranking guide 30 and corresponding descriptive ranking guide 40 for the NPUAP Pressure Ulcer Staging System. However, first arm 12 further includes an abbreviated descriptive ranking guide 59 for "Other" skin problems. The abbreviated ranking guide 59 may simply include, for example, rank title indicators and appropriate spacers 58, as discussed below. Generally speaking, all skin wounds may be divided into either pressure wounds, which may then be categorized as indicated above, or "Other" types of wounds, which have their own categorization system. The "Other" categorization system has three ranks for wounds, which may be labeled superficial, partial thickness and full thickness. Rank classifier indicia for the "superficial" rank include intact skin with redness of a localized area or damage to the epidermis layer of skin. Rank classifier indicia for "partial thickness" include damage to the epidermis and dermis layers of the skin; such damage may be superficial and presents as a red, smooth, shallow crater, abrasion or serum-filled blister. Rank classifier indicia for "full thickness" include damage through the skin to the subcutaneous layer of skin and even to the structures of muscle tendon or bone; it may present as a deep crater and may even tunnel into surrounding subcutaneous tissue.

As shown in FIG. 2, the abbreviated descriptive ranking guide 59 of the second classification system may be positioned and designed so as to align with the graphical ranking guide 30 of the first classification system; in this manner rank classifier indicia common to both systems may be beneficially employed on the tool 10. For example, as shown in the tool 10, one or more images 32 from one or more ranks in a finely-grained first classification system may be shared to illustrate a single rank in a coarsely-grained second classification system 59. The appropriate grouping of images 32 for each rank in the coarsely-grained second classification system 59 may be indicated by spacers 58 or the like, such as arrows or any other suitable grouping indicator.

Figure 4:
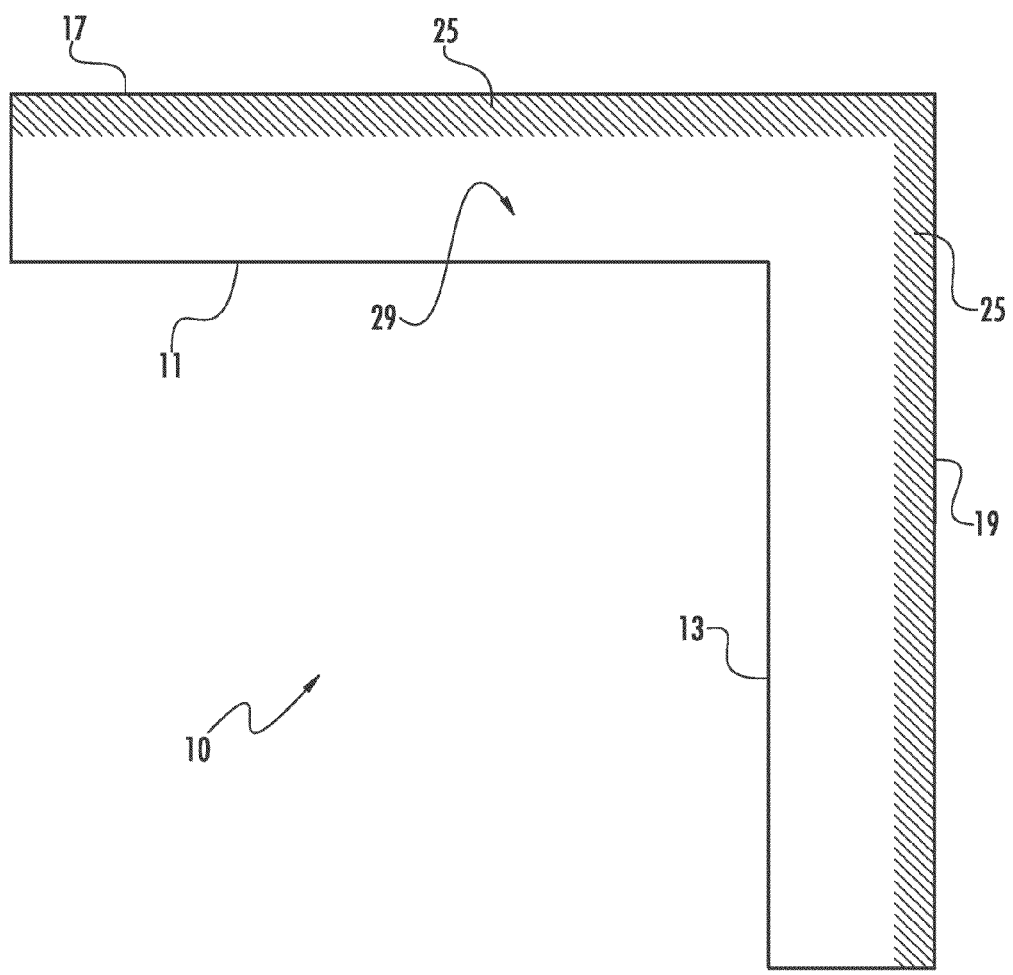
FIG. 4 is a bottom schematic view of the device shown in FIG. 1.

FIG. 4 shows the bottom surface 29 of the embodiment tool 10. As illustrated in FIG. 4, the bottom surface 29 of the substrate 20 preferably includes a low-tack, pressure sensitive adhesive 25, such as is used on sticky notes, EKG electrodes, transdermal drug patches and the like. Other tacky surfaces may be used, such as silicone, or no tacky surfaces may be used if there is a known allergy to adhesive or silicone products. Any suitable adhesive may be used as known in the art. The tool 10 preferably meets guidelines and is labeled as a "latex free" product. In preferred embodiments the adhesive 25 is a strip approximately 20 cm long and 4 cm wide that runs immediately adjacent to the external edges 17, 19 of the substrate 20. It will be appreciated, however, that other placements and locations of the adhesive 25 are possible. For example, the adhesive 25 could be positioned to run adjacent to the internal edges 11, 13 of the substrate 20. Or, the adhesive 25 may cover the entire bottom surface 29.

Figure 5:
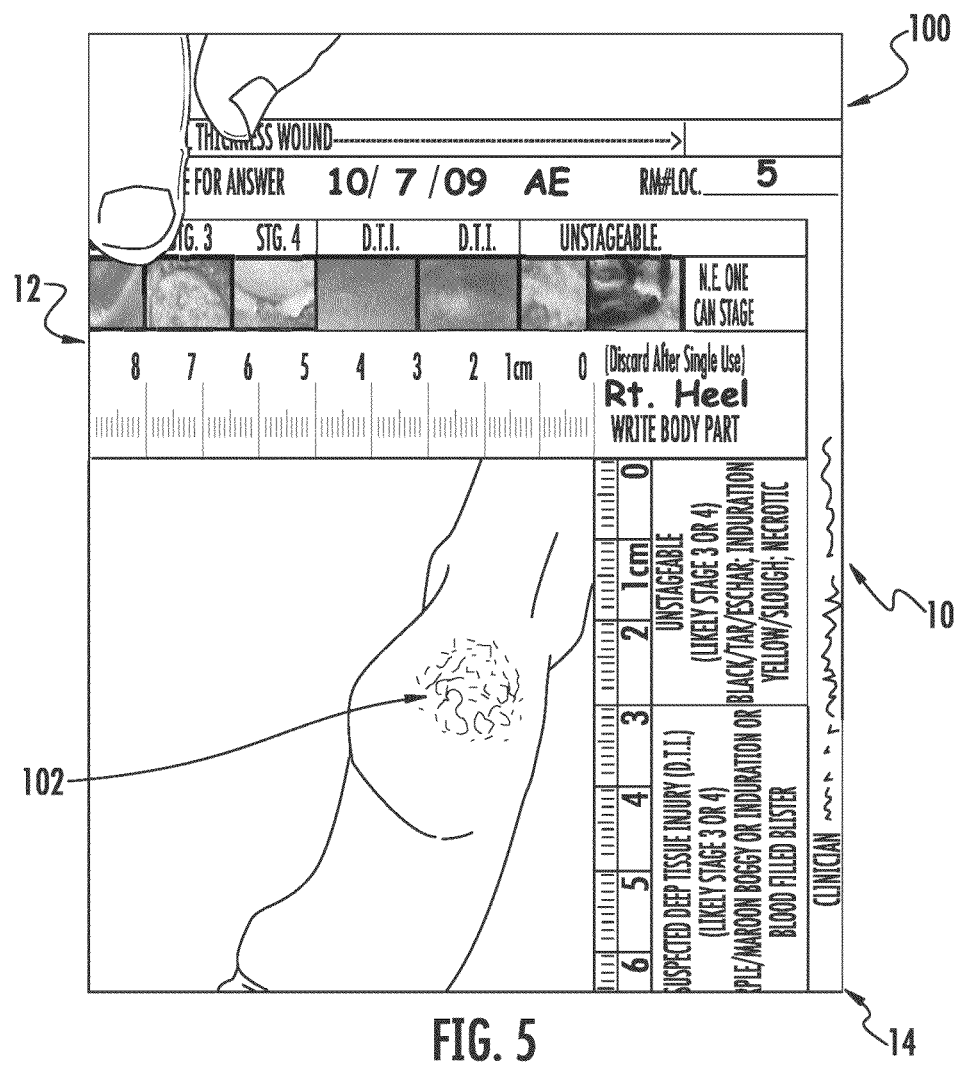
FIG. 5 illustrates use of the diagnostic classification assessment tool with a subject in accordance with one embodiment disclosed within this specification.

FIG. 5 illustrates how the embodiment tool 10 may be used with a subject 100. With further reference to FIG. 5, the tool 10 may be positioned so that the arms 12, 14 extend around, but do not touch, an affliction 102 of a subject 100. It will be appreciated that the adhesive 25 on the bottom surface 29 of the tool 10 may assist in such placement, and keeps the tool 10 in position while, for example, a photograph is being taken. The practitioner may refer to the graphical ranking guide 30 and select a rank for the affliction based upon the graphical image 32 and descriptor 42 that most closely match the affliction 102, as optionally suggested by instructions 51. The practitioner may then record his or her assessment of the ranked value for the affliction 102 on, for example, the tool itself in a suitable field, or by circling the appropriate rank title indicator or image 32, by entry of the value into a separate form or the like. The practitioner may further record other relevant information where indicated, such as date, practitioner name, affliction location and so forth directly onto the related fields on the top surface 21.

Figure 6:
FIG. 6 illustrates a method employing the diagnostic classification assessment tool in accordance with one embodiment disclosed within this specification.

FIG. 6 illustrates a particularly preferred method for using the embodiment tool 10. In a preferred embodiment method, the practitioner positions the tool 10 in contact with the subject to extend around the affliction 102 as described above, and then takes a picture of the affliction 102 with the tool 10 visible in the picture around the affliction 102. It will be appreciated that the adhesive 25 keeps the tool 10 in contact with the subject, which is convenient for the photography step. Preferably at least the internal origin 16, the first ruler 22 and second ruler 24 are visible in the resultant picture, together with the affliction 102 itself. The picture is then printed in any standard manner and the resultant print 202, which is preferably a color print, is affixed to a form 200, such as with tape, glue, staples or the like, which may then be incorporated into a chart for the subject 100. The print 202 may be used to assist a practitioner in the filling out of fields on the form 200, and provides clear, intuitive evidence of the affliction 102 and the bases for any analysis and diagnosis present in the form 200. Further, as indicated in FIG. 6, a practitioner may mark up the print 202 with lines extending perpendicularly from the arms 12, 14 to the extreme extents of the affliction 102 to approximately assess the surface area of the affliction 102.

Particularly preferred embodiment tools 10 are made from a paper substrate 20, and all graphical and textual information present on the top surface 21 is provided by any suitable printing process, preferably a color printing process to support color graphical images 32. A plurality of such tools 10 may be stacked together, such a stack being mutually held together by the adhesive 25 on the back of each tool 10, much like common sticky notes (i.e., Post-It® notes), the top tool 10 being peeled off of the stack for use. After single patient use, each tool 10 may then be discarded.

It will be appreciated that, with specific reference to the embodiment tool 10, any hospital employee that has passed competencies for correctly filling out the tool 10 information (date 52, patient initials 53, body part 56, room/location 54, photographer's signature 57, etc.), correct placement on the subject 100 and correct photographing techniques can then provide the picture 202 for the patient's medical record 200. The data captured in the photo 202 may provide valuable information for the appropriate practitioner to assess, fill out additional documentation, begin appropriate interventions and diagnosis within their scope of practice. It will also be appreciated that reliable, objective facts are consequently made available in the medical record 200 from correct use of the tool 10. In turn this may facilitate ease for timely choosing correct treatment and prevention interventions, chart coding and for litigation purposes.

It will be further understood that tools 10 may be adapted for different classification systems. The graphical ranking guide 30 and descriptive ranking guide 40 may thus be changed to conform to such other classification systems, thereby illustrating representative rank classifier indicia for each rank in the classification system, and optionally providing corresponding instructions 51. For example, the graphical ranking guide 30 and descriptive ranking guide 40 could be reconfigured to show images and corresponding text illustrative of the various ranks in the burn classification system, the Wagner's Scale for foot ulcers, the Payne Martin Classification for skin tears and so forth.

There is an increasing push to move away from paper to all-electronic filing and docketing. This is particularly true in the medical context. To facilitate this, certain embodiments provide a camera that electronically incorporates a virtual rendering of the above-described assessment tool over the photograph being taken, thereby eliminating the need of the actual physical substrate 20.

Cameras that can take pictures and then determine the scale of items displayed in the resultant photograph are known. For example, U.S. Pat. No. 5,969,822 entitled "Arbitrary-Geometry Laser Surface Scanner," the contents of which are incorporated herein by reference in their entirety, discloses a three-dimensional scanning system that may be handheld and records the position of objects. U.S. published application number 2009/0213213, published Aug. 27, 2009, and entitled "Method of Monitoring a Surface Feature and Apparatus Therefore," the contents of which are incorporated herein by reference in their entirety, discloses a device capable of capturing a surface feature and determining a scale associated with the image. Indeed, handheld devices that permit a user to see the scale of the image taken, and electronically measure the area of a region within the image, are on the market, such as the Silhouette Mobile device from ARANZ Medical Limited of New Zealand.

Figure 7:
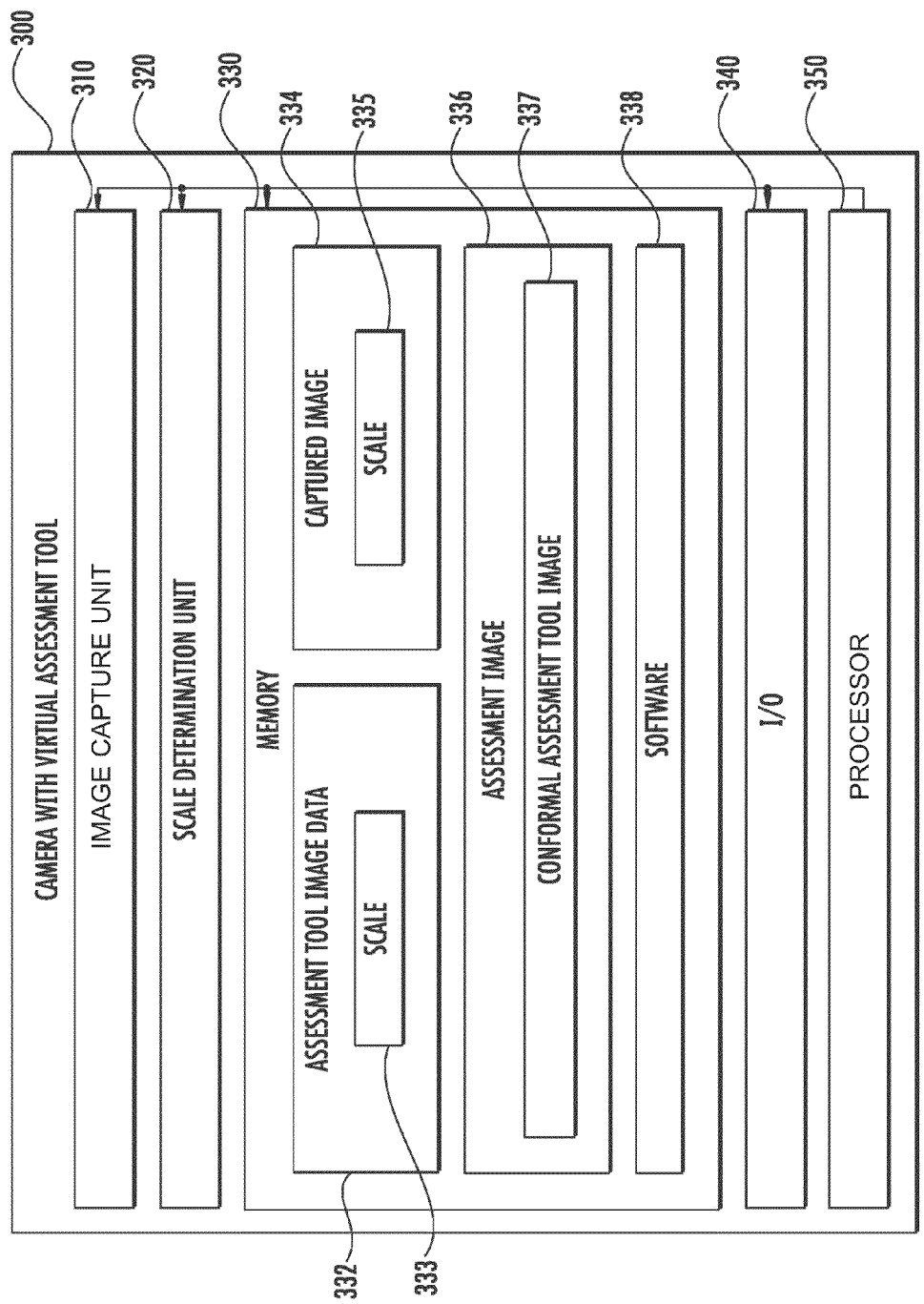
FIG. 7 is a functional diagram of a diagnostic imaging system in accordance with one embodiment disclosed within this specification.
Figure 8A:
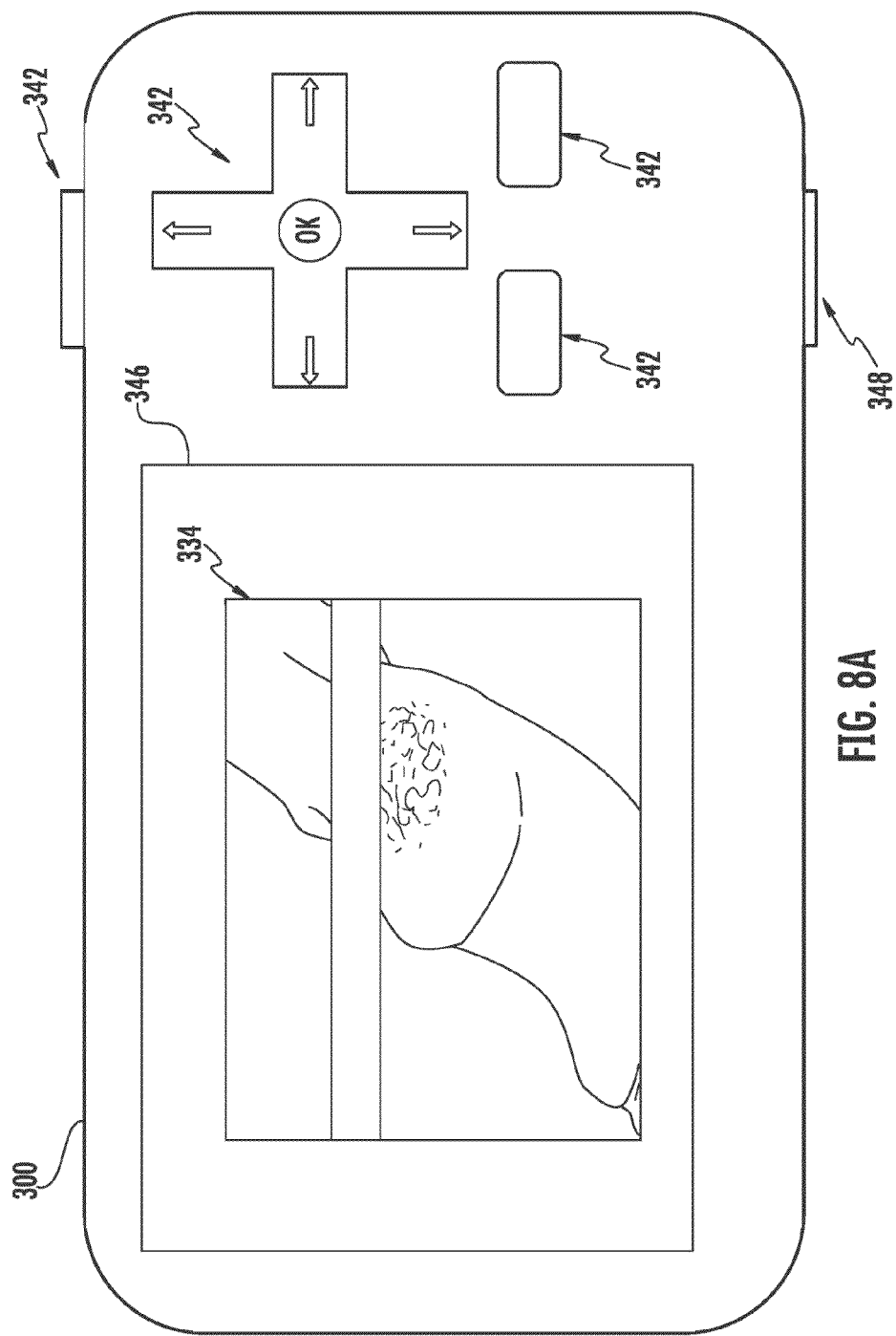
Figure 8B:
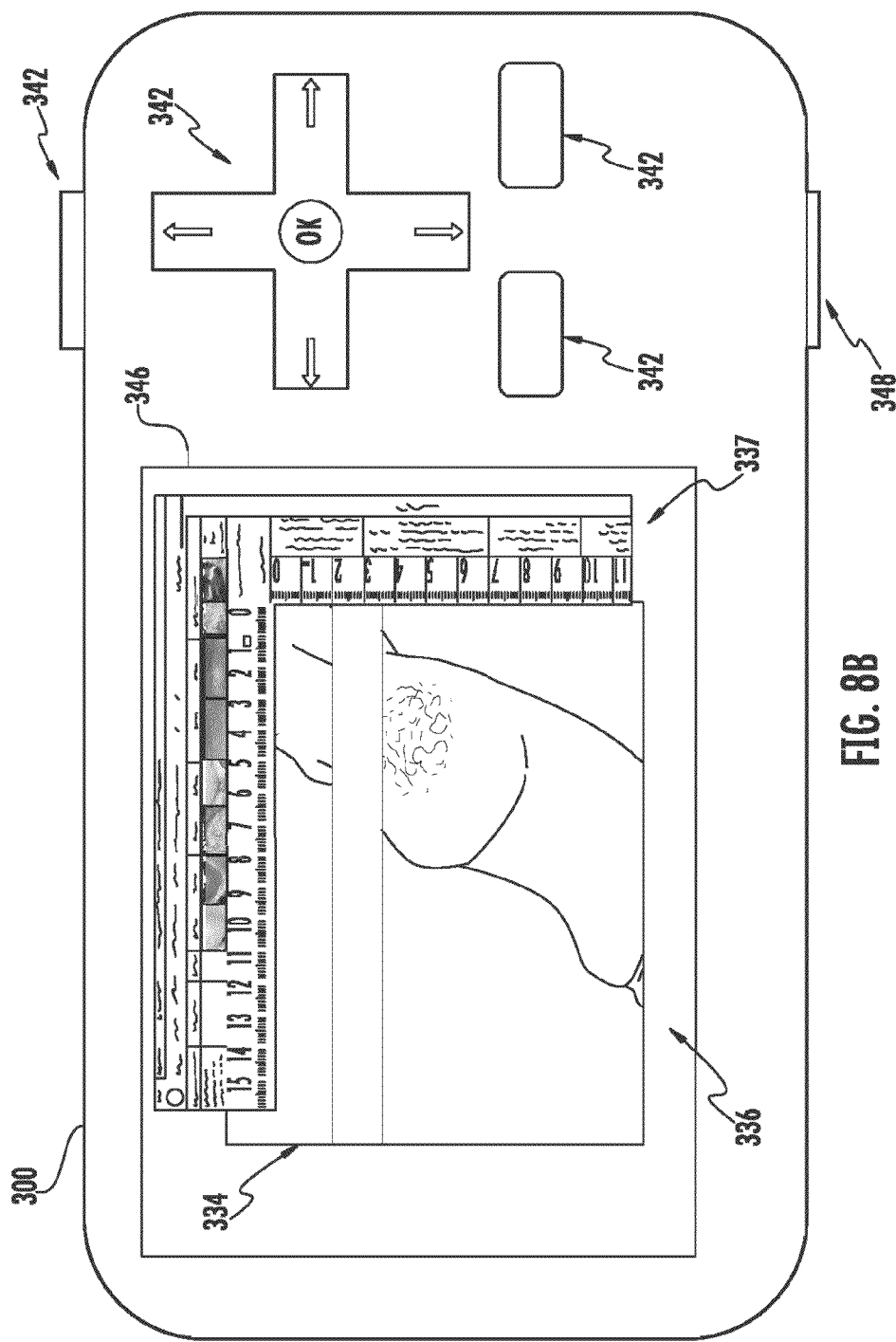

FIG. 7 is a functional diagram of a diagnostic imaging system (hereinafter "system") 300 in accordance with one embodiment disclosed within this specification. FIGS. 8A-8C depict back views of the system 300 with image manipulation being performed by a user according to an embodiment assessment method. The system 300 uses known image capturing and scale determination technology to capture an image and then introduce into that image a virtual representation of the assessment tool discussed above at a scale that is consistent with the determined scale of the image. The system 300 can include an image capture unit 310, a scale determination unit 320, memory 330, an input/output (I/O) interface 340 and a processor 350, for example a central processing unit (CPU) or other suitable processor.

The image capture unit 310 includes all the components needed to capture an image and store a digital representation of the image 334 in the memory 330; such components may include, for example, a light capturing device, such as a CCD or the like; an optical focusing unit including lenses, a lens driving motor, and the like. Any suitable image capture unit 310 may be used.

The scale determination unit 320 determines the scale 335 of the image 334 captured by the image capturing system 310. Any suitable scale determination system 320 may be used. In one arrangement, the scale determination unit 320 may include, for example, one or more lasers to create a predetermined pattern within the view of the image capture unit 310, optional sensors to determine the tilt of the system 300, and so forth, and may also include software 338 within the memory 330 that is program code executable by the processor 350 to process collected data and apply an algorithm to obtain the scale 335, which is then stored in the memory 330. In another arrangement, the scale determination unit 320 can be a module of program code executable by the processor 350 to process captured images and identify one or more dimensions of objects contained in the captured images, as will be described herein.

The memory 330 can include one or more machine-readable storage mediums. A machine-readable storage medium may include a volatile memory and/or a non-volatile memory, and is used to store data and software 338 executable by the processor 350 to provide the functionality of the system 300 as described above and in the following. Volatile memory can refer to, for example, random access memory (RAM) or other non-persistent memory device(s) generally used during actual execution of the program code. Non-volatile memory may be implemented as an electronic, magnetic, optical, electromagnetic, infrared, or semiconductor system, apparatus, or device, or any suitable combination of the foregoing. For example, a non-volatile memory can be implemented as a hard disk drive (HDD), solid state drive (SSD), a portable computer diskette, a read-only memory (ROM), an erasable programmable read-only memory (EPROM or Flash memory), a portable compact disc read-only memory (CD-ROM), a digital versatile disc (DVD), or the like.

For example, as indicated the software 338 may include algorithms to obtain the captured image scale 335. The software 338 may also include program code to control the I/O 340 to support a suitable user interface for the system 300. Finally, the software 338 may include code to generate an assessment image 336 that includes at least a portion of the assessment tool 110 and the wound to which the assessment tool 110 is proximally located, the assessment tool 110 comprising at least the first arm 112, the first arm 112 depicting measurement indicators to which a size of the wound is correlated. The assessment too further can comprise the second arm 114 depicting additional measurement indicators to which the size of the wound in correlated.

The virtual representation of the embodiment of the portion of the assessment tool superimposed onto the image 334 captured by the image capture unit 310 can be presented at a scale or size that is conformal to the scale 335 of the captured image 336. To this end the memory 330 further can include data 332 representative of an embodiment assessment tool. For example, this may be an actual image 332 of an embodiment assessment tool, or a portion of the assessment tool, such as the tool 10, or may be data that is processed by the processor 350 to generate such an image. This assessment tool image data 332 further can include a scale 333 that indicates the scale of the assessment image data 332.

The I/O 340 may include buttons 342, a display 346 (which may be touch sensitive), a speaker, plugs, data ports 348 (i.e, USB, FireWire®, Bluetooth, etc.) and the like to support a user interface and the exchange of data with other devices, as known in the art.

The processor 350 is in communications with the I/O 340, the memory 330, the scale determination unit 320 and the image capture unit 310 and executes software 338 to support and control the various units 310-340, to provide a user interface and to provide the overall functionality of the system 300. Any suitable software 338 may be employed to provide the functionality as described herein, and coding such software 338 should be well within the means of one having ordinary skill in the art after having the benefits of this disclosure.

Upon receipt of a signal via the I/O interface 340 to take a picture, the processor 350 can direct the image capture unit 310 and the scale determination unit 320 to respectively take a photograph and to determine the scale of the resultant image 334. The image 334 and its scale 335 are then stored in the memory 330. The image 334 may be presented on the display 346, as shown in FIG. 8A. Then, such as in response to a user request via the I/O interface 340, the processor 350 can compare the scale 335 of the image 334 to the scale 333 of the virtual assessment tool 332 and perform linear scaling of the assessment tool image data 332 to generate a conformal assessment tool image 337 that is at a scale that equals or substantially equals (i.e., within display tolerances or user viewing tolerances) the scale 335 of the captured image 334. Any suitable image processing algorithm may then be employed by the processor 350 to superimpose the conformal assessment tool image 337 onto the captured image 334 to thereby generate the assessment image 336. The assessment image 336 may be presented on the display 346, as shown in FIG. 8B, in which the assessment tool image 337 is initially presented in a predetermined location relative to the captured image 334, such as in the upper right hand corner of the captured image 334.

As indicated in FIG. 8C, in one embodiment, the user interface 342, 346 may permit the user to move the conformal image 337 around the captured image 334, using any suitable image manipulation techniques and user interfaces, to determine the final positioning of the virtual assessment tool image 337 with respect to the captured image 334; once the user is satisfied with the final position, indicated for example via a suitable signal with the I/O 340, the processor 350 generates the final assessment image 336 with the conformal assessment tool 337 positioned thereon as desired by the user. This assessment image 336 may finally replace the originally captured image 334, or may be stored in the memory 330 together with the captured image 334.

It will be appreciated that in some embodiments the system 300 may permit the user to enter alpha-numeric data via the I/O interface 340, which can then be used to fill in forms or fields in the virtual assessment tool image 337. Hence, data entered by the user into the system 300 may appear within the assessment tool image 337 on the final assessment image 336. This final assessment image 336 may then be downloaded into another device via the data port 348 for printing, insertion into an electronic file or the like.

Figure 9:
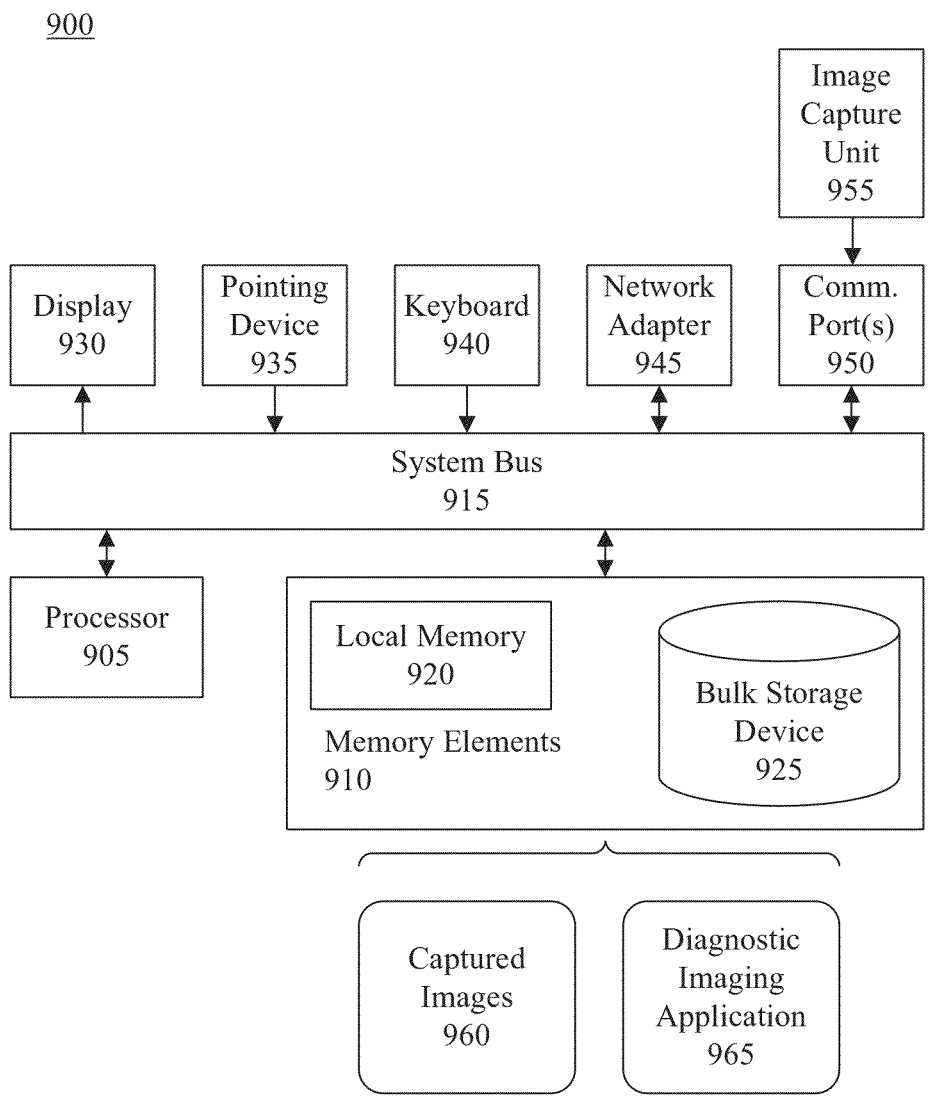
FIG. 9 is a functional diagram of a diagnostic imaging system in accordance with another embodiment disclosed within this specification.

FIG. 9 is a functional diagram of a diagnostic imaging system (hereinafter "system") 900 in accordance with another embodiment disclosed within this specification. The system 900 can include at least one processor 905 (e.g., a central processing unit) coupled to memory elements 910 through a system bus 915 or other suitable circuitry. As such, the system 900 can store program code within the memory elements 910. The processor 905 can execute the program code accessed from the memory elements 910 via the system bus 915. It should be appreciated that the system 900 can be implemented in the form of any system including a processor and memory that is capable of performing the functions and/or operations described within this specification. For example, the system 900 can be implemented as a computer, a workstation, a mobile computer, a laptop computer, tablet computer, a smart phone, a personal digital assistant, an appliance, and so on.

The memory elements 910 can include one or more machine-readable storage mediums (i.e., physical memory devices) such as, for example, local memory 920 and one or more bulk storage devices 925. Local memory 920 refers to volatile memory, such as RAM or other non-persistent memory device(s) generally used during actual execution of the program code. The bulk storage device(s) 925 can be implemented as non-volatile memory, such as an electronic, magnetic, optical, electromagnetic, infrared, or semiconductor system, apparatus, or device, or any suitable combination of the foregoing. Examples of bulk storage devices 925 include, but are not limited to, a hard disk drive (HDD), solid state drive (SSD), a portable computer diskette, a read-only memory (ROM), an erasable programmable read-only memory (EPROM or Flash memory), a portable compact disc read-only memory (CD-ROM), a digital versatile disc (DVD), or the like. The system 900 also can include one or more cache memories (not shown) that provide temporary storage of at least some program code in order to reduce the number of times program code must be retrieved from the bulk storage device 925 during execution.

Input/output (I/O) devices such as a display 930, a pointing device 935 and, optionally, a keyboard 940 can be coupled to the system 900. The I/O devices can be coupled to the system 900 either directly or through intervening I/O controllers. For example, the display 930 can be coupled to the system 900 via a graphics processing unit (GPU), which may be a component of the processor 905 or a discrete device. One or more network adapters 945 also can be coupled to system 900 to enable system 900 to become coupled to other systems, computer systems, remote printers, and/or remote storage devices through intervening private or public networks. Modems, cable modems, transceivers, and Ethernet cards are examples of different types of network adapters 945 that can be used with system 900. Further, one or more communication ports 950 may be coupled to the system 900. Examples of suitable communication ports include, but are not limited to, a universal serial bus (USB) port, an IEEE-1394 (FireWire®) port, a serial ATA (SATA) port, a small computer system interface (SCSI) port, a wireless communication port (e.g., a Bluetooth® transceiver), and the like.

In one arrangement, the system 900 can include an image capture unit 955. The image capture unit 955 can include components configured to capture one or more images 960 and store digital representations of the images 960 in the memory elements 910; such components may include, for example, a light capturing device, such as a CCD or the like; an optical focusing unit including lenses, a lens driving motor, and the like. Any suitable image capture unit 955 may be used.

In another arrangement, the image capture unit 955 can be a separate device or system, for example a digital camera, and the system 900 can receive images 960 captured by the image capture unit 955 via the communication port(s) 950. In one aspect, the system 900 can receive the images 960 directly from the image capture unit 955, and store such images 960 to the memory elements 910. In another aspect, the image capture unit 955 can store the images to a computer-readable storage medium (not shown), such as a portable storage device, and the system 900 can receive the images 960 from the computer-readable storage medium. Again, the system 900 can store such images 960 to the memory elements 910.

As pictured in FIG. 9, the memory elements 910 further can store a diagnostic imaging application 965. Being implemented in the form of executable program code, the diagnostic imaging application 965 can be executed by the system 900 (e.g., by the processor 905) to process captured images 960, as will be described herein. As such, the diagnostic imaging application 965 can be considered part of the system 900. Moreover, the diagnostic imaging application 965 and images 960 are functional data structures that impart functionality when employed as part of the system 900 of FIG. 9.

Figure 10:
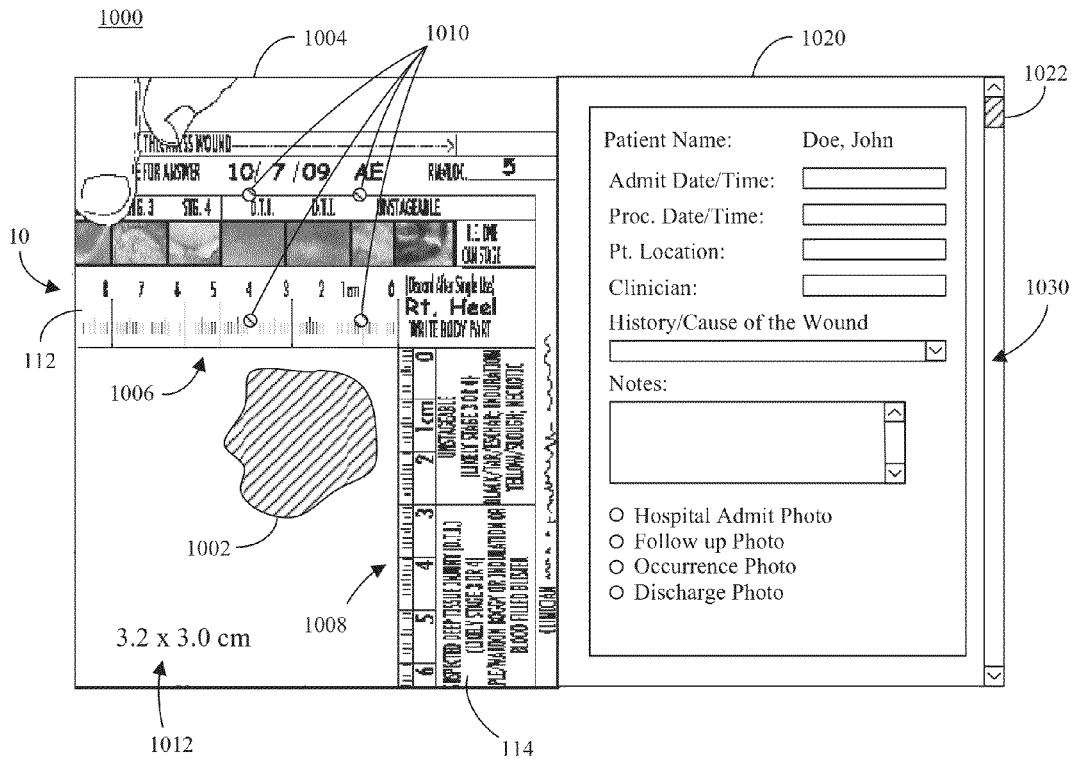
FIG. 10 depicts a view presented by the diagnostic imaging system of FIG. 9 in accordance with an embodiment disclosed within this specification.

FIG. 10 depicts a view 1000 presented by the diagnostic imaging system 900 of FIG. 9 on the display 930 in accordance with an embodiment disclosed within this specification. In operation, the image capture unit 955 can capture an image 960, comprising at least a portion of the assessment tool 10 of FIG. 1 and an affliction (e.g., a wound) 1002 to which the assessment tool is proximally located, and generate corresponding image data. The image data can be processed by the processor 905 to present an assessment image 1004 in the view 1000. The assessment image 1004 can include the entire captured image 960 or a portion of the captured image 960. In this regard, the assessment image 1004 can include at least a portion of the assessment tool 10 of FIG. 1 and the affliction 1002 to which the assessment tool 10 is proximally located.

As noted, the first arm 112 of the assessment tool 10 can depict measurement indicators 1006 to which a size of the affliction 1002 is correlated, and the second arm the second arm 114 can depict additional measurement indicators 1008 to which the size of the affliction 1002 in correlated. The measurement indicators can depicted as, for example, rulers on the respective first and second arms 112, 114. In another aspect, in addition to or in lieu of the measurement indicators 1006, 1008, measurement indicators 1010 can be depicted on the assessment tool 10. The measurement indicators 1010 can be, for example, dots presented on the first arm 112 and/or second arm 114 of the assessment tool 10. The measurement indicators 1010 can be depicted on the assessment tool 10 at the time the assessment tool 10 is manufactured, or added sometime later, for example using adhesive stickers. The measurement indicators 1010 can be spaced apart at particular distances, thus providing a dimensional reference for image processing.

In operation, the processor 905 can perform image processing on the captured image 960 to identify the affliction 1002 in the captured image and compare at least one dimension of the affliction 1002 to the measurement indicators 1106, 1008 and/or 1010 to determine the size of the affliction 1002. In one arrangement, different types of assessment tools may be used, and the measurement indicators 1106, 1008 and/or 1010 may differ among various assessment tools. A user can be prompted to indicate the type of assessment tool 10 depicted in the assessment image 1004, and the processor 905 can identify a correlation between the size of the affliction 1002 and the measurement indicators 1106, 1008 and/or 1010 based on the indicated type of tool 10.

In one arrangement, the processor can present an annotation 1012 in the view 1000, or elsewhere on the display 930, indicating the size of the affliction 1002. Further, based on the size of the affliction 1002, identified based on correlation between the size of the affliction and the measurement indicators 1106, 1008 and/or 1010, the processor 905 can automatically assign a medical score to the affliction.

The system 900 also can present in the view 1000, or in a separate view, one or more forms 1020 to receive user inputs entering data and/or selecting at least one field presented in the view 1000 related to the patient, the affliction, etc. The form 1020 can include a plurality of fields configured to receive the user inputs, for example text entry fields, drop down menus, selectable icons, buttons, radio buttons, and the like, for example in a first portion 1030 of the form 1020. The form can include a scroll bar 1022 via which the user can navigate to various portions of the form 120.

Figure 11:
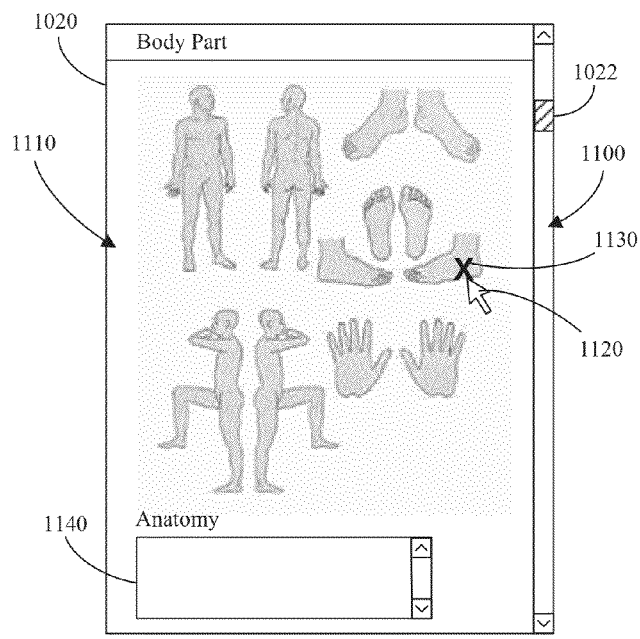
FIGS. 11-13 depict various portions of a form presented in a view in accordance with an embodiment disclosed within this specification.

FIG. 11 depicts another portion 1100 of the form 1020, to which the user can navigate using the scroll bar 1022. The portion 1100 can depict various images 1110 of a human body. Using the pointing device 935, a user can move a curser 1120 to a particular portion of an image 1110 and select that portion of the image 1110 to indicate that is where the affliction 1002 is present on the patient. In illustration, when the user selects that portion of the image 1110 with the curser 1120, a marker 1130 can be placed over that portion. The user can select, move and/or delete the marker 1130 as the user so chooses. Further, a field 1140 can be provided for the user to enter notes pertaining to the anatomy of where the affliction 1002 is located on the patient.

Figure 12:
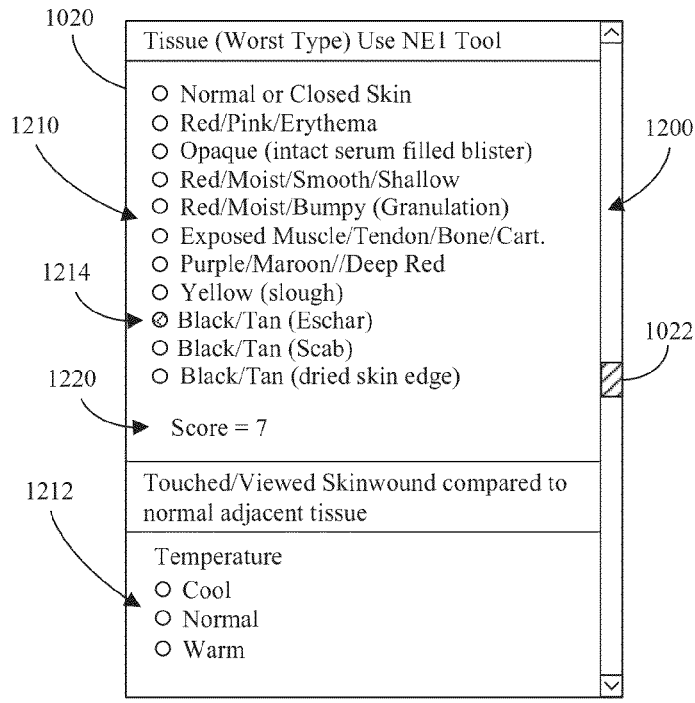

FIG. 12 depicts another portion 1200 of the form 1020, to which the user can navigate using the scroll bar 1022 or navigate to in another suitable manner. The portion 1200 can present a plurality of user selectable affliction classifiers 1210, 1212. Affliction classifiers 1210, 1220 corresponding to the patient's affliction 1002 can be selected by the user using buttons, radio buttons, selectable icons, or the like. In one arrangement, one or more medical scores 1220 can be assigned to the affliction 1002 based on the selected affliction classifiers 1210, 1212 and presented in the form 1020. In illustration, if the user selects a particular affliction classifier 1214, a corresponding medical score 1220 can be automatically assigned to the affliction.

Figure 13:
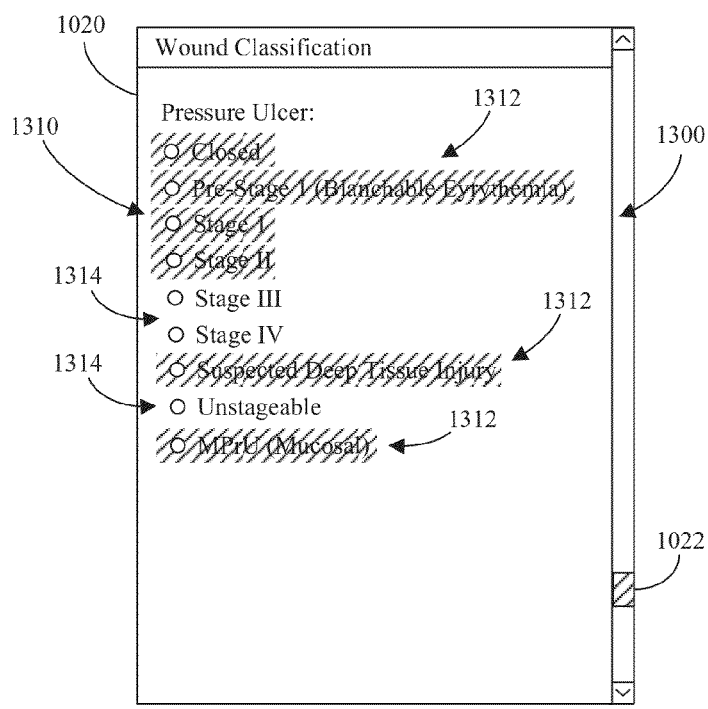

FIG. 13 depicts another portion 1300 of the form 1020, to which the user can navigate using the scroll bar 1022 or navigate to in another suitable manner. The portion 1300 can present another plurality of user selectable affliction classifiers 1310. In one arrangement, the plurality of user selectable affliction classifiers 1310 that are presented in the portion 1300 of the form 1020 can be affliction classifiers that potentially correspond to one or more of the affliction classifiers 1210, 1220 selected in the portion 1200 of the form 120.

Further, affliction classifiers 1312 that are not applicable to the affliction, based on previous user selections made in the form 1020 or elsewhere in the system, can be indicated as not being applicable to the affliction 1002. For instance, the affliction classifiers 1312 that are not applicable can be highlighted with a particular color (e.g., grayed out), or presented in another suitable manner that distinguishes the non-applicable affliction classifiers 1312 from potentially applicable affliction classifiers 1314. Further, the buttons, radio buttons, selectable icons, etc. can be disabled for the affliction classifiers 1312 to prevent the user from being able to select them. In another arrangement, affliction classifiers 1312 that are not applicable need not be presented in the form 1020. Regardless, affliction classifiers 1314 that potentially may be applicable to the affliction 1002, based on previous user selections made in the form 1020 or elsewhere in the system, can be presented in the form 1020 in a manner in which the affliction classifiers 1314 are user selectable.

At this point it should be noted that the form 1020 can include various other portions configured to receive user inputs related to the patient and the affliction 1002. Moreover, rather than all portions being presented in a single form, a plurality of forms can be presented. The plurality of forms can be presented to the user sequentially as the user proceeds through a process of filling out the forms and/or accessed via a menu presented to the user.

Figure 14:
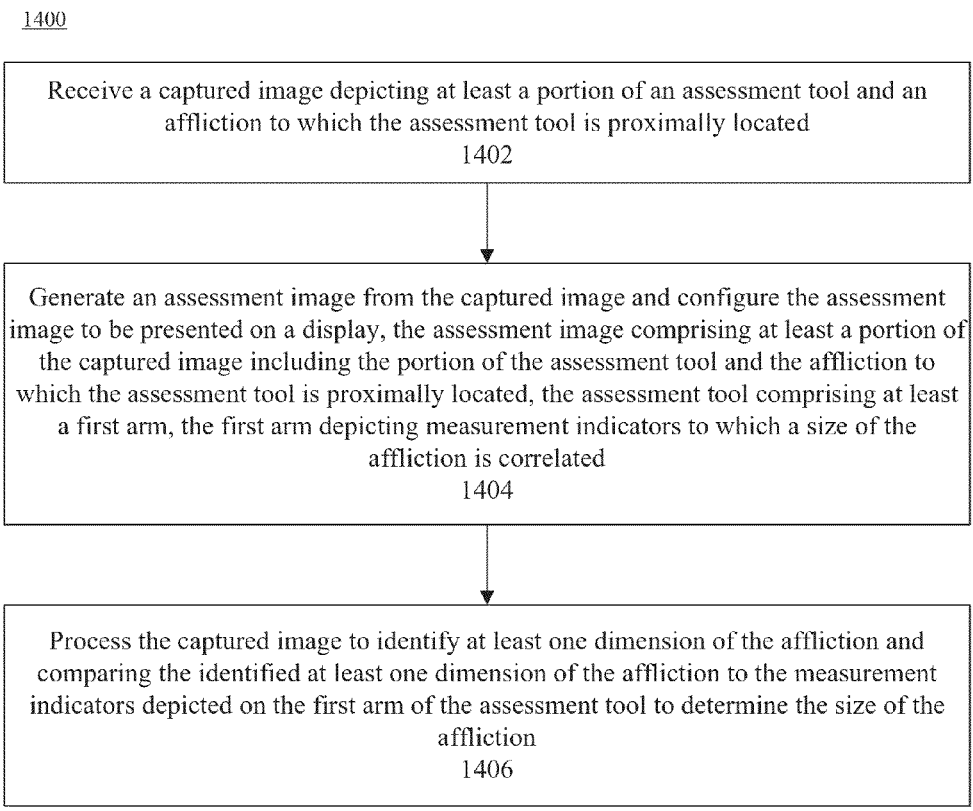
FIG. 14 is a flowchart presenting a method of processing a captured image in accordance with an embodiment disclosed within this specification.

FIG. 14 is a flowchart presenting a method 1400 of processing a captured image in accordance with an embodiment disclosed within this specification. At step 1402, a captured image can be received. The captured image can depict at least a portion of an assessment tool and an affliction to which the assessment tool is proximally located.

At step 1404, an assessment image can be generated from the captured image. The assessment image can be configured to be presented on a display. The assessment image can include at least a portion of the captured image including the portion of the assessment tool and the affliction to which the assessment tool is proximally located. The assessment tool can include at least a first arm, the first arm depicting measurement indicators to which a size of the affliction is correlated.

At step 1406, the captured image can be processed to identify at least one dimension of the affliction and comparing the identified at least one dimension of the affliction to the measurement indicators depicted on the first arm of the assessment tool to determine the size of the affliction.

Like numbers have been used to refer to the same items throughout this specification. The flowcharts and block diagrams in the figures illustrate the architecture, functionality, and operation of possible implementations of systems, methods and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or other apparatus adapted for carrying out the methods described herein is suited. A typical combination of hardware and software can be a processing system with computer-usable or computer-readable program code that, when being loaded and executed, controls the processing system such that it carries out the methods described herein. The systems, components and/or processes also can be embedded in a computer-readable storage medium, such as a computer-readable storage medium of a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

The terms "computer program," "software," "application," variants and/or combinations thereof, in the present context, include any expression, in any language, code or notation, of a set of instructions intended to cause a system having an information processing capability to perform a particular function either directly or after either or both of the following: a) conversion to another language, code or notation; b) reproduction in a different material form. For example, an application can include, but is not limited to, a script, a subroutine, a function, a procedure, an object method, an object implementation, an executable application, an applet, a servlet, a MIDlet, a source code, an object code, a shared library/dynamic load library and/or other sequence of instructions designed for execution on a processing system.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Reference throughout this specification to "one embodiment," "an embodiment," "one arrangement," "an arrangement," or similar language means that a particular feature, structure, or characteristic described in connection with the embodiment is included in at least one embodiment disclosed within this specification. Thus, appearances of the phrases "in one embodiment," "in an embodiment," "in one arrangement," "in an arrangement," and similar language throughout this specification may, but do not necessarily, all refer to the same embodiment or arrangement.

The term "plurality," as used herein, is defined as two or more than two. The term "another," as used herein, is defined as at least a second or more. The term "coupled," as used herein, is defined as connected, whether directly without any intervening elements or indirectly with one or more intervening elements, unless otherwise indicated. Two elements also can be coupled mechanically, electrically, or communicatively linked through a communication channel, pathway, network, or system. The term "and/or" as used herein refers to and encompasses any and all possible combinations of one or more of the associated listed items. It will also be understood that, although the terms first, second, etc. may be used herein to describe various elements, these elements should not be limited by these terms, as these terms are only used to distinguish one element from another unless stated otherwise or the context indicates otherwise.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The corresponding structures, materials, acts, and equivalents of all means or step plus function elements in the claims below are intended to include any structure, material, or act for performing the function in combination with other claimed elements as specifically claimed. The description of the embodiments disclosed within this specification have been presented for purposes of illustration and description, but are not intended to be exhaustive or limited to the form disclosed. Many modifications and variations will be apparent to those of ordinary skill in the art without departing from the scope and spirit of the embodiments of the invention. The embodiments were chosen and described in order to best explain the principles of the invention and the practical application, and to enable others of ordinary skill in the art to understand the inventive arrangements for various embodiments with various modifications as are suited to the particular use contemplated.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

What is claimed is:

1. A diagnostic imaging system comprising:
   a processor programmed to initiate executable operations comprising:
   receiving a captured image depicting at least a portion of an assessment tool and an affliction to which the assessment tool is proximally located;
   generating an assessment image from the captured image and configuring the assessment image to be presented on a display, the assessment image comprising at least a portion of the captured image including the portion of the assessment tool and the affliction to which the assessment tool is proximally located, the assessment tool comprising at least a first arm, the first arm depicting measurement indicators to which a size of the affliction is correlated; and
   processing the captured image to identify at least one dimension of the affliction and comparing the identified at least one dimension of the affliction to the measurement indicators depicted on the first arm of the assessment tool to determine the size of the affliction.

2. The diagnostic imaging system of claim 1, further comprising:
   an image capture unit configured to capture the image depicting at least the portion of the assessment tool and the affliction to which the assessment tool is proximally located.

3. The diagnostic imaging system of claim 1, the executable operations further comprising:
   presenting an annotation on the display with the presented image, the annotation indicating the size of the affliction.

4. The diagnostic imaging system of claim 1, the executable operations further comprising:
   identifying the correlation between the size of the affliction and the measurement indicators and, based on the identified correlation, assigning a medical score to the affliction.

5. The diagnostic imaging system of claim 1, the executable operations further comprising:
   prompting a user to indicate a type of the assessment tool; and
   identifying a correlation between the size of the affliction and the measurement indicators based on the indicated type of the assessment tool.

6. The diagnostic imaging system of claim 1, the executable operations further comprising:
   presenting on the display, proximate to the assessment image, at least one view comprising a plurality of fields that prompt a user to enter or select information related to the affliction;
   receiving from the user at least one user input corresponding to the affliction; and
   storing the at least one user input to the at least one computer-readable storage medium as affliction assessment data.

7. The diagnostic imaging system of claim 1, wherein the assessment tool further comprises at least a second arm, the second arm depicting additional measurement indicators to which the size of the affliction in correlated, the executable operations further comprising:
   processing the captured image to identify at least a second dimension of the affliction and comparing the identified at least second dimension of the affliction to the additional measurement indicators depicted on the second arm of the assessment tool to determine the size of the affliction.

8. The diagnostic imaging system of claim 1, the executable operations further comprising:
   presenting at least one form on the display, the form configured to receive user inputs related to the affliction;
   receiving at least one user input entering data into a field of the form or selecting a user selectable field of the form; and
   based on the user input, automatically assigning a medical score to the affliction.

9. The diagnostic imaging system of claim 1, the executable operations further comprising:
   presenting at least one form on the display, the form configured to receive user inputs related to the affliction;
   receiving at least one user input selecting at least a first user selectable field presented in the form; and
   based on the user input selecting the first user selectable field, automatically presenting at least a second user selectable field in the form that corresponds to the first user selectable field.

10. The diagnostic imaging system of claim 1, the executable operations further comprising:
    presenting at least one form on the display, the form configured to receive user inputs related to the affliction;
    receiving at least one user input selecting at least a first user selectable field presented in the form; and
    based on the user input selecting the first user selectable field, automatically distinguishing at least a second field presented in the form that is not applicable to the affliction from at least a third field presented in the form that is applicable to the affliction.

11. A method comprising:
    receiving a captured image depicting at least a portion of an assessment tool and an affliction to which the assessment tool is proximally located;

generating an assessment image from the captured image and configuring the assessment image to be presented on a display, the assessment image comprising at least a portion of the captured image including the portion of the assessment tool and the affliction to which the assessment tool is proximally located, the assessment tool comprising at least a first arm, the first arm depicting measurement indicators to which a size of the affliction is correlated; and processing, using a processor, the captured image to identify at least one dimension of the affliction and comparing the identified at least one dimension of the affliction to the measurement indicators depicted on the first arm of the assessment tool to determine the size of the affliction.

12. The method of claim 11, further comprising:
presenting an annotation on the display with the presented image, the annotation indicating the size of the affliction.

13. The method of claim 11, further comprising:
identifying the correlation between the size of the affliction and the measurement indicators and, based on the identified correlation, assigning a medical score to the affliction.

14. The method of claim 11, further comprising:
prompting a user to indicate a type of the assessment tool; and
identifying a correlation between the size of the affliction and the measurement indicators based on the indicated type of the assessment tool.

15. The method of claim 11, further comprising:
presenting on the display, proximate to the assessment image, at least one view comprising a plurality of fields that prompt a user to enter or select information related to the affliction;
receiving from the user at least one user input corresponding to the affliction; and
storing the at least one user input to the at least one computer-readable storage medium as affliction assessment data.

16. The method of claim 11, wherein the assessment tool further comprises at least a second arm, the second arm depicting additional measurement indicators to which the size of the affliction in correlated, the method further comprising:
processing the captured image to identify at least a second dimension of the affliction and comparing the identified at least second dimension of the affliction to the additional measurement indicators depicted on the second arm of the assessment tool to determine the size of the affliction.

17. The method of claim 11, further comprising:
presenting at least one form on the display, the form configured to receive user inputs related to the affliction;
receiving at least one user input entering data into a field of the form or selecting a user selectable field of the form; and
based on the user input, automatically assigning a medical score to the affliction.

18. The method of claim 11, further comprising:
presenting at least one form on the display, the form configured to receive user inputs related to the affliction;
receiving at least one user input selecting at least a first user selectable field presented in the form; and
based on the user input selecting the first user selectable field, automatically presenting at least a second user selectable field in the form that corresponds to the first user selectable field.

19. The method of claim 11, further comprising:
presenting at least one form on the display, the form configured to receive user inputs related to the affliction;
receiving at least one user input selecting at least a first user selectable field presented in the form; and
based on the user input selecting the first user selectable field, automatically distinguishing at least a second field presented in the form that is not applicable to the affliction from at least a third field presented in the form that is applicable to the affliction.

20. A computer program product, the computer program product comprising a computer-readable storage medium having program code stored thereon, the program code executable by a processor to perform a method comprising:
receiving, by the processor, a captured image depicting at least a portion of an assessment tool and an affliction to which the assessment tool is proximally located;
generating, by the processor, an assessment image from the captured image and configuring the assessment image to be presented on a display, the assessment image comprising at least a portion of the captured image including the portion of the assessment tool and the affliction to which the assessment tool is proximally located, the assessment tool comprising at least a first arm, the first arm depicting measurement indicators to which a size of the affliction is correlated; and
processing, by the processor, the captured image to identify at least one dimension of the affliction and comparing the identified at least one dimension of the affliction to the measurement indicators depicted on the first arm of the assessment tool to determine the size of the affliction.

* * * * *